(12) United States Patent
Yeon et al.

(10) Patent No.: US 9,091,661 B2
(45) Date of Patent: Jul. 28, 2015

(54) METHOD AND APPARATUS FOR MEASURING DAMAGE TO AN ORGANIC LAYER OF A THIN FILM ENCAPSULATION

(71) Applicant: SAMSUNG DISPLAY CO., LTD., Yongin, Gyeonggi-do (KR)

(72) Inventors: Ki-Young Yeon, Yongin (KR); Na-Ri Ahn, Yongin (KR); Kang-Hyun Kim, Yongin (KR); Jung-Hwa Park, Yongin (KR)

(73) Assignee: Samsung Display Co., Ltd., Giheung-Gu, Yongin, Gyeonggi-Do (KR)

( * ) Notice: Subject to any disclaimer, the term of this patent is extended or adjusted under 35 U.S.C. 154(b) by 6 days.

(21) Appl. No.: 14/040,626

(22) Filed: Sep. 28, 2013

(65) Prior Publication Data

US 2014/0320853 A1  Oct. 30, 2014

(30) Foreign Application Priority Data

Apr. 25, 2013  (KR) .......................... 10-2013-0046205

(51) Int. Cl.
*G01N 21/88* (2006.01)
*G01N 21/84* (2006.01)

(52) U.S. Cl.
CPC ............ *G01N 21/88* (2013.01); *G01N 21/8422* (2013.01); *G01N 2021/8438* (2013.01)

(58) Field of Classification Search
USPC ............... 356/237.1–237.5; 250/474.1, 458.1
See application file for complete search history.

(56) References Cited

U.S. PATENT DOCUMENTS

| | | | |
|---|---|---|---|
| 5,781,445 A | 7/1998 | Shiue et al. | |
| 6,495,833 B1 * | 12/2002 | Alfano et al. | 250/341.8 |
| 2003/0193672 A1 * | 10/2003 | Okada et al. | 356/630 |
| 2004/0068132 A1 * | 4/2004 | Lecloux et al. | 556/18 |
| 2005/0035305 A1 * | 2/2005 | Kleinfeld et al. | 250/458.1 |
| 2005/0041243 A1 * | 2/2005 | Choo et al. | 356/239.1 |
| 2009/0159817 A1 * | 6/2009 | Irie et al. | 250/474.1 |
| 2009/0219523 A1 * | 9/2009 | Morris et al. | 356/300 |
| 2009/0324970 A1 * | 12/2009 | Ito | 428/442 |
| 2011/0207244 A1 * | 8/2011 | Sung et al. | 438/7 |
| 2011/0278603 A1 * | 11/2011 | Miyazawa et al. | 257/88 |

FOREIGN PATENT DOCUMENTS

| | | |
|---|---|---|
| KR | 10-2005-0017070 A | 2/2005 |
| KR | 10-2011-0000818 A | 1/2011 |
| KR | 10-2011-0133115 A | 12/2011 |

\* cited by examiner

*Primary Examiner* — Sang Nguyen
(74) *Attorney, Agent, or Firm* — Robert E. Bushnell, Esq.

(57) ABSTRACT

A method of measuring damage of an organic layer of a thin film encapsulation includes: preparing a thin film encapsulation structure in which an inorganic layer is stacked on an organic layer, in which a light-emitting material is mixed; irradiating light to the thin film encapsulation structure so that light is emitted from the light-emitting material, the intensity of light emitted from the light emitting material decreasing over time; detecting a light emission lifetime of the light emitted from the light emitting material; and determining a degree of damage to the organic layer based on the light emission lifetime. Accordingly, a degree of the damage to the organic layer due to plasma may be easily detected, and the damage to the organic layer may be minimized based on the detected degree of the damage by improving plasma process conditions for an operation of forming an inorganic layer.

11 Claims, 4 Drawing Sheets

METHOD AND APPARATUS FOR MEASURING DAMAGE TO AN ORGANIC LAYER OF A THIN FILM ENCAPSULATION

CLAIM OF PRIORITY

This application makes reference to, incorporates the same herein, and claims all benefits accruing under 35 U.S.C. §119 from an application for METHOD AND APPARATUS FOR MEASURING DAMAGE TO AN ORGANIC LAYER OF A THIN FILM ENCAPSULATION, earlier filed in the Korean Intellectual Property Office on Apr. 25, 2013, and there duly assigned Serial No. 10-2013-0046205.

BACKGROUND OF THE INVENTION

1. Field of the Invention

The present invention relates to a method and apparatus for measuring the extent of damage to an organic layer included in a thin film encapsulation of an organic light-emitting display device.

2. Description of the Related Art

An organic light-emitting display device typically includes a display unit in which an emissive layer formed of an organic material is interposed between an anode electrode and a cathode electrode. When a voltage is applied between the anode electrode and the cathode electrode, holes implanted into the anode electrode and electrons implanted into the cathode electrode recombine in the emissive layer to generate excitons, and light is emitted as the excitons transfer from an excited state to a ground state, thereby forming an image.

Importantly, if the emissive layer of the display unit directly contacts water, the light-emitting characteristics thereof deteriorate, and, thus, the display unit may be covered with an encapsulation member in order to prevent this. A stacked thin film encapsulation formed by alternately stacking at least one organic layer and at least one inorganic layer has been frequently used as an encapsulation member. Among the stacked layers constituting the thin film encapsulation, the function of preventing penetration of moisture into the display unit is performed mainly by the inorganic layer(s), and the function of giving flexibility to the thin film encapsulation is performed by the organic layer(s).

However, when an organic layer and an inorganic layer are stacked adjacent to each other, the organic layer may frequently be damaged. That is, while an inorganic layer is typically formed by using a plasma process, an underlying organic layer, which is formed in advance, may also be affected by the plasma and deteriorate, and thus defects in the organic layer, such as progressive dark points, may occur frequently. This may cause significant adverse effects in the product reliability of an organic light-emitting display device (OLED). However, there has heretofore been no method to check the degree of damage caused by exposure of an organic layer in a thin film encapsulation to plasma. Such a method would enable an OLED fabricator to handle this problem.

Accordingly, a method of determining the degree of damage to an organic layer in a thin film encapsulation due to plasma exposure is necessary in order to provide an OLED fabricator with means for determining ways of mitigating this damage.

SUMMARY OF THE INVENTION

The present invention provides a method and apparatus for detecting a degree of damage to an organic layer in a thin film encapsulation, the damage being caused by exposure of the organic layer to a plasma.

According to an embodiment of the present invention, there is provided a method of measuring damage to an organic layer of a thin film encapsulation, the method including: preparing a thin film encapsulation structure in which an inorganic layer is stacked on an organic layer, in which a light-emitting material is mixed; irradiating light to the thin film encapsulation structure so that light is emitted from the light-emitting material, the intensity of light emitted from the light-emitting material decreasing over time; detecting a light emission lifetime of the light emitted from the light emitting material; and determining a degree of damage to the organic layer based on the light emission lifetime.

The inorganic layer may be formed on the organic layer using a plasma process.

When the organic layer is damaged by plasma, one of carbonyl, carboxyl, and hydroxyl groups may be generated.

The organic layer may include one of an epoxy-based material and an acrylic material.

It may be determined that the shorter the lifetime for emission of light from the light emitting material, the more is the organic layer damaged by the plasma.

The light-emitting material may include a phosphorescent material.

The light-emitting material may include a fluorescent material.

According to another embodiment of the present invention, there is provided an apparatus for measuring damage to an organic layer of a thin film encapsulation, the apparatus including: a light-irradiating unit for irradiating light to the thin film encapsulation structure in which an inorganic layer is stacked on an organic layer, in which a light-emitting material is mixed; a light-receiving unit for detecting a light emission lifetime of the light emitted from the light-emitting material, the intensity of light emission from the light emitting material decreasing over time; and a controller for determining a degree of damage to the organic layer based on the light emission lifetime.

The light-irradiating unit may include a light source unit and a confocal microscopy system that adjusts a depth at which light emitted from the light source unit is focused.

The light source unit may include a light source and an optical parametric amplifier (OPA) that converts a wavelength of the light emitted from the light source to an excitation wavelength that stimulates light emission from the light-emitting material.

The light source may include at least one of a femtosecond pulse laser and a nanosecond pulse laser.

The light source unit may include one of a short wavelength laser and a lamp.

The light-receiving unit may include a filter that blocks light reflected from the thin film encapsulation structure, a monochromator that forms the light received from the light-emitting material into monochromatic light, and a sensor that measures a variation in intensity of the monochromatic light.

The sensor may include one of a charge-coupled device (CCD)-photomultiplier tube (PMT), a PMT, and a photodiode.

BRIEF DESCRIPTION OF THE DRAWINGS

A more complete appreciation of the invention and many of the attendant advantages thereof will be readily apparent as the same becomes better understood by reference to the following detailed description when considered in conjunction with the accompanying drawings in which like reference symbols indicate the same or similar components, wherein.

DETAILED DESCRIPTION OF THE INVENTION

Figure 1:
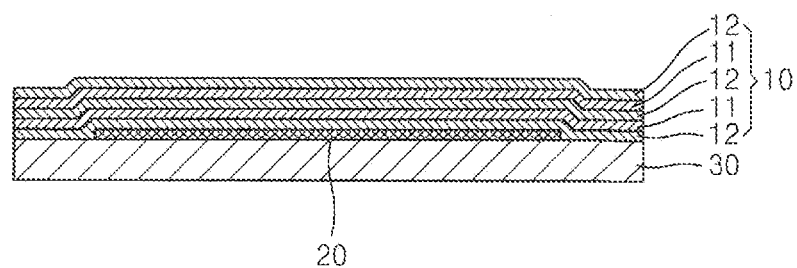
FIG. 1 is a cross-sectional view illustrating an organic light-emitting display device including a thin film encapsulation, according to an embodiment of the present invention.

Hereinafter, an exemplary embodiment of the present invention will be described in detail with reference to the accompanying drawings.

In the drawings, like reference numerals denote like elements. In the description of the present invention, certain detailed explanations of related art are omitted when it is deemed that they may unnecessarily obscure the essence of the invention.

In the drawings, the thicknesses of layers and regions are exaggerated for clarity. It will also be understood that when a layer, film, region, or plate is referred to as being "on" another layer, film, region, or plate, it can be directly on the other layer, film, region, or plate, or intervening layers may also be present.

Figure 2:
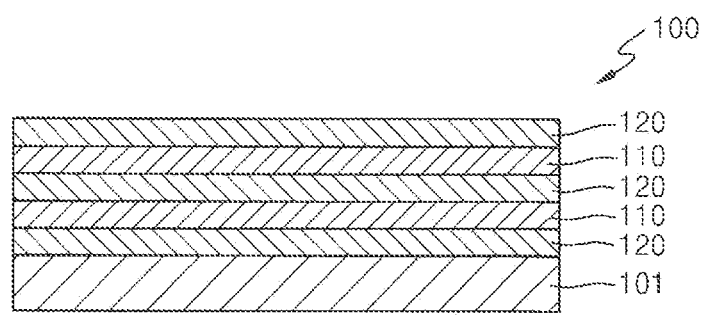
FIG. 2 is a cross-sectional view illustrating a thin film encapsulation structure for performing a method of measuring damage to an organic layer, according to an embodiment of the present invention.
Figure 3:
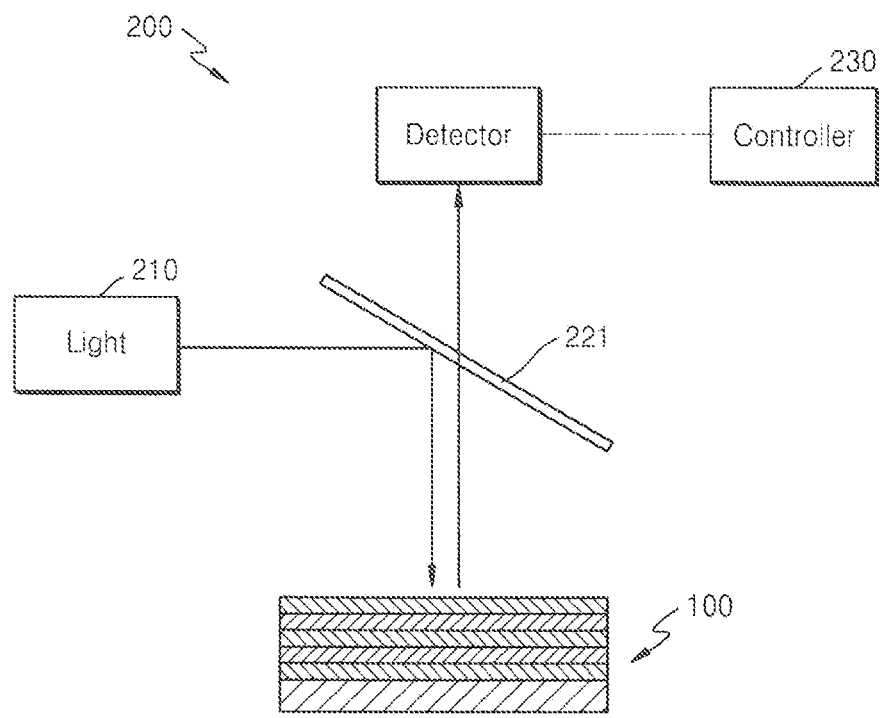
FIG. 3 is a structural diagram illustrating an apparatus for measuring damage to an organic layer, according to an embodiment of the present invention.

FIG. 1 is a cross-sectional view illustrating an organic light-emitting display device including a thin film encapsulation, according to an embodiment of the present invention. FIG. 2 is a cross-sectional view illustrating a thin film encapsulation structure 100 for performing a method of measuring damage of an organic layer, according to an embodiment of the present invention. FIG. 3 is a structural diagram illustrating an apparatus for measuring damage to an organic layer, according to an embodiment of the present invention.

First, referring to FIG. 1, the organic light-emitting display device may include a display unit 20 that is disposed on a substrate 30 and forms an image, and an organic layer 11 and an inorganic layer 12 may be alternately stacked on the display unit 20 as a thin film encapsulation 10. Accordingly, the display unit 20 may be encapsulated between the substrate 30 and the thin film encapsulation 10, and the thin film encapsulation 10 may protect the display unit 20 from external moisture and air. The function of preventing penetration of moisture is mainly performed by the inorganic layer 12, and the organic layer 11 performs the function of giving flexibility to the thin film encapsulation 10.

As described above, when the organic layer 11 and the inorganic layer 12 are alternately stacked, damage whereby dark points are caused in the organic layer 11 occurs frequently. That is, a deposition process using plasma is performed when forming the inorganic layer 12, and this plasma damages the organic layer 11, which has been formed in advance. Accordingly, in order to reduce damage to the organic layer 11, conditions for a plasma process have to be adjusted, and, to that end, a degree of the damage, that is, how much the organic layer 11 is damaged by plasma, has to be exactly determined.

According to the current embodiment of the present invention, a method of accurately determining a degree of damage to the organic layer 11 in the thin film encapsulation 10 is provided as follows:

First, the thin film encapsulation structure 100 as illustrated in FIG. 2 may be prepared as a measurement object. The thin film encapsulation structure 100 may have a structure in which an organic layer 110 and an inorganic layer 120 are alternately stacked, that is, only the organic layer 110 and the inorganic layer 120 are formed, on a substrate 101, in order to measure a degree of damage of the organic layer 110 without any image forming element, such as a display unit. Here, the inorganic layer 120 may also be formed by using a deposition operation using plasma, and the organic layer 110 may be damaged in this deposition operation to some extent.

The organic layer 110 may be formed of an epoxy-based material or an acrylic material that generates one of carbonyl, carboxyl, and hydroxyl groups as a byproduct when it is damaged by plasma. In addition, a light-emitting material (not shown) that is excited upon light radiation to emit light, such as a phosphorescent material or a fluorescent material, may be mixed in the organic layer 110. Accordingly, when light is irradiated to the organic layer 110, the light-emitting material may emit light for a predetermined period of time. Among the phosphorescent material and the fluorescent material, the phosphorescent material has far better reactivity with respect to the byproduct, and thus is more suitable to be used in measurement of the damage by plasma according to the current embodiment of the present invention, and an iridium (Ir)-based material may be used as a phosphorescent material. In addition, a passivation layer formed of LiF may be directly formed on the substrate 101, though this is not necessarily included.

When the thin film encapsulation structure 100 for the measurement is prepared, the thin film encapsulation structure 100 may be mounted to a measuring unit 200, as illustrated in FIG. 3.

The measuring unit 200 may measure a degree of damage by plasma of the organic layer 100 included in the thin film encapsulation structure 100. The measuring unit 200 includes a light-irradiating unit 210, a light-receiving unit 220, and a controller 230 or the like.

Figure 4:
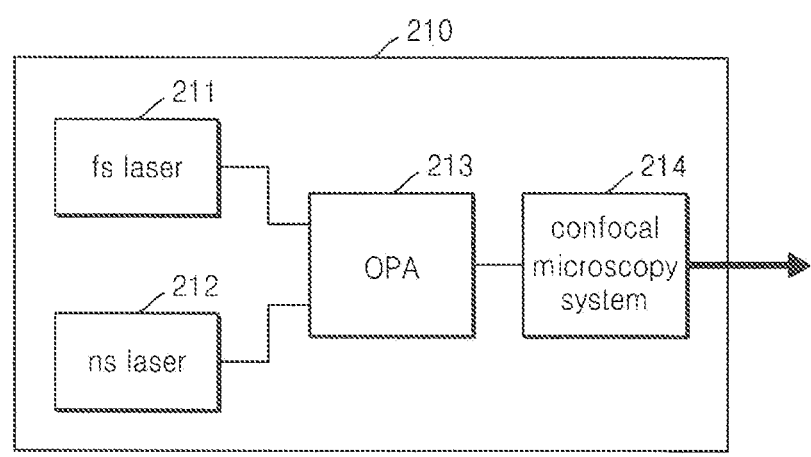
FIG. 4 is a structural diagram illustrating in more detail the light-irradiating unit shown in FIG. 3 according to an embodiment of the present invention.

First, the light-irradiating unit 210 may provide light to excite the light-emitting material contained in the organic layer 110 of the thin film encapsulation structure 100. As illustrated in FIG. 4, the light-irradiating unit 210 may include a light source unit, which in turn may include a femtosecond pulse laser 211 and a nanosecond pulse laser 212 as light sources and an optical parametric amplifier (OPA) 213 that may convert a wavelength of the light sources to an excitation wavelength that stimulates light emission from the light-emitting material. In addition, the light-irradiating unit 210 may further include a confocal microscopy system 214 that may adjust a depth at which the converted light is focused within the thin film encapsulation structure 100. Accordingly, when laser is emitted from the femtosecond pulse laser 211 and the nanosecond pulse laser 212, the OPA 213 may convert a wavelength of the light to an excitation wavelength that stimulates light emission from the light-emitting material, and the light of the excitation wavelength may be irradiated to an organic layer formed at a depth to be measured by using the confocal microscopy system 214. Instead of the femtosecond pulse laser 211 and the nanosecond pulse laser 212, a simple lamp or a monochromatic laser may be used. However, using the femtosecond pulse laser 211 and the nanosecond pulse laser 212 together may allow adjustment of the light source unit to produce any of a large number of excitation wavelengths, and, thus, various phosphorescent materials may be used as light emitting materials. If a simple lamp or a monochromatic laser is used, a phosphorescent material of a predetermined fixed type corresponding to an excitation wavelength that may be produced from the lamp or monochromatic laser has to be used.

Figure 7:
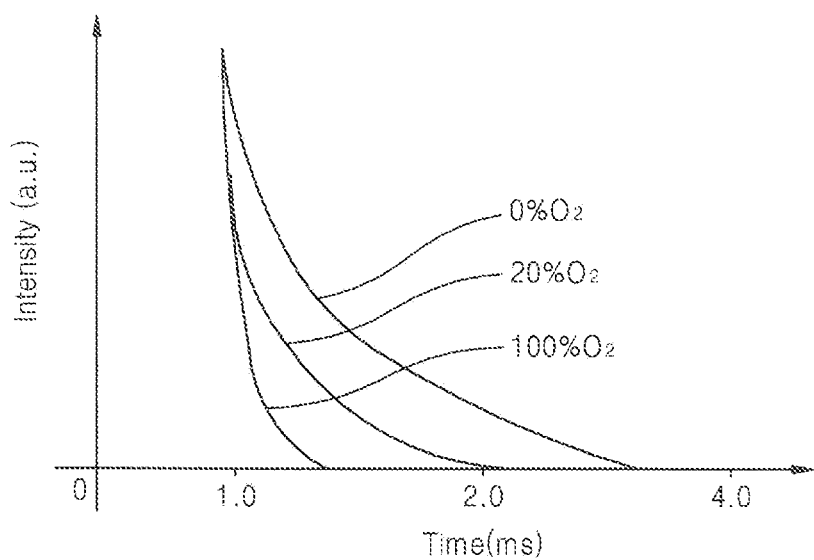
FIG. 7 is a graph showing a tendency of a light emission lifetime of an emissive material mixed in an organic layer to decrease in the presence of an oxygen-containing functional group in the organic layer relative to the light emission lifetime of the emissive material in an undamaged organic layer.

When light is irradiated from the light irradiating unit, the light-emitting material in the organic layer 110 that corresponds to the depth setting defined by the confocal microscopy system 214 may be excited so as to emit light, the light emitted by the light emitting material may be received by the light-receiving unit 220, and the controller 230 may then process the data received from the light-receiving unit 220 to calculate a light emission lifetime and to relate the light emission lifetime to a degree of damage to the examined organic layer 110. FIG. 7 is a graph showing how a light emission lifetime of an emissive material mixed in an organic layer corresponds to a level of oxygenation of the organic layer, the light emission lifetime decreasing as the level of oxygen-containing functional groups increases. In certain embodiments of the present invention, the light is emitted for a short period of time to gradually shimmer with a decreasing intensity, and this time period of light emission is referred to as a light emission lifetime. As illustrated in FIG. 7, the higher the content of oxygen, the shorter the light emission lifetime of the light-emitting material, and, as described above, carbonyl, carboxyl, and hydroxyl groups generated in the organic layer 110 by the plasma may give rise to reduced light emission lifetimes. Accordingly, it may be determined that the shorter the light emission lifetime, the more the organic layer 110 is damaged.

Figure 5:
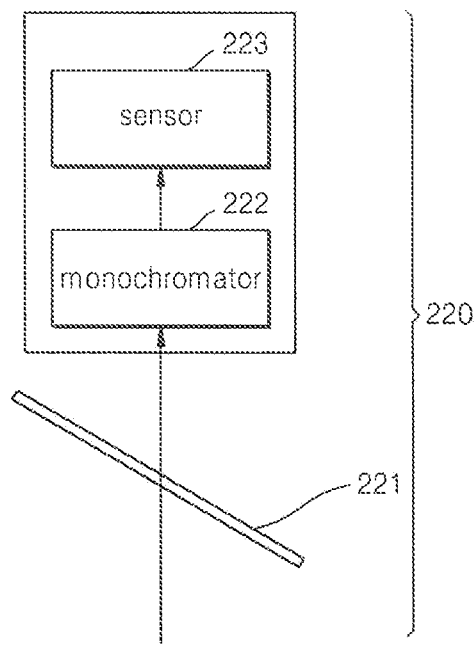
FIG. 5 is a structural diagram illustrating in more detail the light-receiving unit illustrated in FIG. 3 according to an embodiment of the present invention.

The light-receiving unit 220 may detect the light emission lifetime, and, as illustrated in FIG. 5, the light-receiving unit 220 may include a polarizing filter 221 that blocks the light from the light irradiating unit that is reflected from the thin film encapsulation structure 100 such that the reflected light does not remain mixed with light that is emitted from the light emitting material and is proceeding to monochromator 222. Monochromator 222, another part of light-receiving unit 220, may remove light that is not of the wavelength that is emitted from the light emitting material, forming the light that is emitted from the light emitting material into monochromatic light. Light-receiving unit 220 may further include sensor 223, which measures a variation in intensity of the monochromatic light. As the sensor 223, one of a charge-coupled device (CCD)-photomultiplier tube (PMT), a PMT and a photodiode may be used. Accordingly, the light emission lifetime, as illustrated in FIG. 7, may be detected by using the sensor 223 of the light-receiving unit 220 to produce the raw data signals and using the controller 230 to process the raw data signals into a light emission lifetime that indicates how much the organic layer 110 is damaged due to plasma oxidation. The shorter the light emission lifetime, the more intense is the indicated damage, and the longer the light emission lifetime, the less is the indicated damage. Then, the damage of the organic layer 110 may be reduced in subsequent OLED fabrication efforts by appropriately improving the plasma process conditions when forming the inorganic layer 120.

Figure 6:
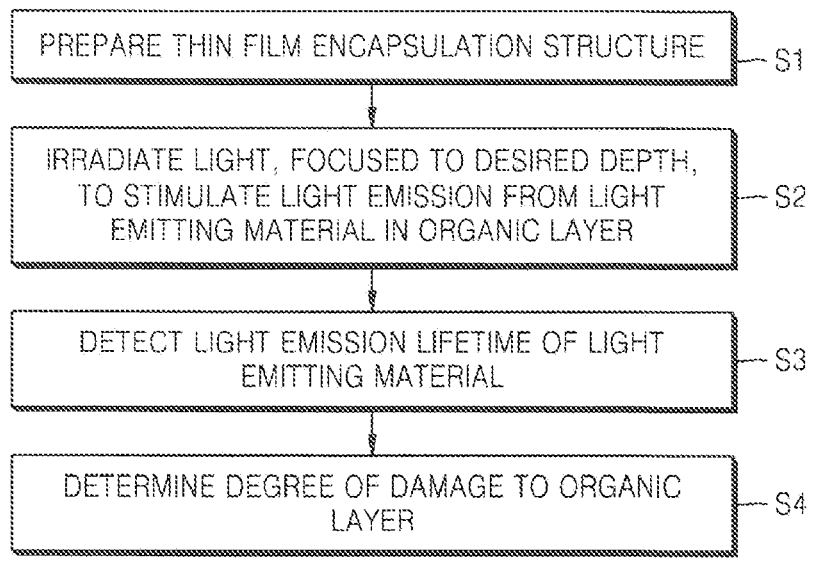
FIG. 6 is a flowchart illustrating a method of measuring damage to an organic layer, according to an embodiment of the present invention.

The method of measuring the extent of damage to an organic layer of a thin film encapsulation as described above may be summed up as below with reference to the flowchart of FIG. 6.

First, as illustrated in FIG. 2, in operation S1, the thin film encapsulation structure 100 in which the inorganic layer 120 is formed on the organic layer 110, a light-emitting material being mixed into the organic layer, may be prepared. The inorganic layer 120 may be formed by using a deposition operation using plasma, and the organic layer 110, which is formed in advance, may be damaged by the plasma. The plasma damage to the organic layer may take the form of carbonyl, carboxyl, and hydroxyl groups that are generated in the organic layer 110, which may be formed of one of an epoxy-based material and an acrylic material, as described above. The oxygen functional groups introduced by the plasma into the organic layer 110 may decrease the light emission lifetime of the light emission material mixed in the organic layer 110.

In operation S2, after the thin film encapsulation structure 100 is prepared, the thin film encapsulation structure 100 may be mounted to the measuring unit 200, as illustrated in FIG. 3, and the light-irradiating unit 210 is driven to irradiate light having a wavelength which may excite the light-emitting material into the organic layer 110.

In operation S3, the light-emitting material mixed in the organic layer 110 may be excited by the light irradiated by the light irradiating unit 210 so as to cause emission of light from the light emitting material, and the light-receiving unit 220 may produce the signal used to calculate the light emission lifetime, which corresponds to the time from the generation of the emitted light to the time when the emitted light disappears.

In operation S4, the controller 230 analyzes the detected light emission lifetime to determine how much the organic layer 110 is damaged. The shorter the light emission lifetime, the more intense is the damage to the examined organic layer.

Accordingly, as the determined data is accumulated, the extent of damage to the organic layer due to plasma exposure may be detected, and damage to the organic layer may be minimized by improving the plasma process conditions when forming an inorganic layer based on the determined data.

Consequently, according to the method and apparatus of measuring a degree of damage to an organic layer of a thin film encapsulation as described above, the degree of damage to the organic layer in the thin film encapsulation due to plasma may be easily detected, and the information inputs needed for deriving process conditions for reducing the damage to the organic layer in actual products may be obtained.

According to the method for measuring damage to an organic layer of a thin film encapsulation as described above, the degree of damage to the organic layer in the thin film encapsulation may be easily detected, and, thus, the means for developing process conditions for reducing damage to the organic layer in actual products may be obtained.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:
1. A method of measuring damage to an organic layer of a thin film encapsulation, the method comprising:

preparing a thin film encapsulation structure in which an inorganic layer is stacked on an organic layer by a plasma process, in which a light-emitting material is mixed;

irradiating light to the thin film encapsulation structure performed by a light-irradiating unit so that light is emitted from the light-emitting material, intensity of the light emitted from the light-emitting material decreasing over time;

detecting a light emission lifetime of the light emitted from the light-emitting material performed by a light-receiving unit; and determining a degree of damage to the organic layer based on the light emission lifetime performed by a controller, wherein the organic layer comprises one of an epoxy-based material and an acrylic material and generates one of carbonyl, carboxyl, and hydroxyl groups when the organic layer is damaged by the plasma process, and the higher the content of the one of carbonyl, carboxyl, and hydroxyl groups, the higher the degree of the damage to the organic layer.

2. The method of claim 1, a higher degree of damage to the organic layer by the plasma being indicated by a shorter light emission lifetime.

3. The method of claim 1, the light-emitting material comprising a phosphorescent material.

4. The method of claim 1, the light-emitting material comprising a fluorescent material.

5. An apparatus for measuring damage to an organic layer of a thin film encapsulation, the apparatus comprising:

a light-irradiating unit for irradiating light to the thin film encapsulation structure in which an inorganic layer is stacked on an organic layer by a plasma process, in which a light-emitting material is mixed;

a light-receiving unit for detecting a light emission lifetime of light emitted from the light-emitting material, intensity of the light emitted from the light emitting material decreasing over time; and a controller for determining a degree of damage to the organic layer based on the light emission lifetime, wherein the organic layer comprises one of an epoxy-based material and an acrylic material and generates one of carbonyl, carboxyl, and hydroxyl groups when the organic layer is damaged by the plasma process, and the higher the content of the one of carbonyl, carboxyl, and hydroxyl groups, the higher the degree of the damage to the organic layer.

6. The apparatus of claim 5, the light-irradiating unit comprising a light source unit and a confocal microscopy system that adjusts a depth at which light emitted from the light source unit is focused.

7. The apparatus of claim 6, the light source unit comprising a light source and an optical parametric amplifier (OPA) that converts a wavelength of the light emitted from the light source to an excitation wavelength that stimulates light emission from the light-emitting material.

8. The apparatus of claim 7, the light source comprising at least one of a femtosecond pulse laser and a nanosecond pulse laser.

9. The apparatus of claim 6, the light source unit comprising one of a short wavelength laser and a lamp.

10. The apparatus of claim 5, the light-receiving unit comprising a filter that blocks light reflected from the thin film encapsulation structure, a monochromator that forms the light received from the light-emitting material into monochromatic light, and a sensor that measures a variation in intensity of the monochromatic light.

11. The apparatus of claim 10, the sensor comprising one of a charge-coupled device (CCD)-photomultiplier tube (PMT), a PMT, and a photodiode.

* * * * *